United States Patent [19]

Simpson

[11] Patent Number: 5,151,074
[45] Date of Patent: Sep. 29, 1992

[54] METHOD OF MANUFACTURING MEDICAL APPLIANCE DISPOSAL CONTAINER

[75] Inventor: James L. Simpson, Indialantic, Fla.

[73] Assignee: Hemox, Inc., Melbourne, Fla.

[21] Appl. No.: 803,105

[22] Filed: Dec. 5, 1991

Related U.S. Application Data

[60] Continuation of Ser. No. 449,675, Dec. 12, 1989, abandoned, which is a division of Ser. No. 300,946, Jan. 24, 1989, Pat. No. 4,927,076.

[51] Int. Cl.⁵ .......................... B31B 3/64; B31B 3/66
[52] U.S. Cl. ................................. 493/133; 493/135; 493/160
[58] Field of Search ....................... 493/59-61, 493/69, 70, 79, 80, 110, 114, 160, 161, 396-404, 901, 912, 129, 133-135

[56] References Cited

U.S. PATENT DOCUMENTS

| | | | |
|---|---|---|---|
| 2,751,136 | 6/1956 | Moore . | |
| 3,394,635 | 7/1968 | Hoyrup et al. | 493/134 |
| 3,447,946 | 6/1969 | Roe, Jr. | 493/148 |
| 3,614,914 | 10/1971 | Troll | 493/133 |
| 3,967,998 | 7/1976 | Kane | 156/226 |
| 4,156,626 | 5/1979 | Souder | 156/273.3 |
| 4,194,440 | 3/1980 | Görg | 493/129 |

Primary Examiner—Bruce M. Kisliuk
Assistant Examiner—Jack Lavinder
Attorney, Agent, or Firm—Evenson, Wands, Edwards, Lenahan & McKeown

[57] ABSTRACT

A medical waste disposal container has a unitary body structure formed of a substantially flat sheet having a plurality of laminated layers of compact fiberboard, and one or more thin pliable layers of absorbtion resistant plastic material. The laminated sheet material contains a plurality of foldable sheet portions that are scored, wrapped at corners and adhesively joined together to define a bottom, sidewalls and a top of the body structure. The top has an opening, that is closeable by way of a flap formed in the sheet material, for insertion of discarded medical waste. The interior of the container is preferably coated with an absorption resistant material to effectively provide a leakproof seal at the intersections of its sidewalls and bottom. Adhesion and additional sealing of the foldable sheet portions is achieved in the course of manufacture by irradiating the laminate sheet material with infrared light, which causes the plastic layer that forms the outer wall surface of the sheet material to become tacky, so that it becomes intimately bonded to an adjacent folded sheet portion to which it is joined, thus securing the wrapeed sheet portions together.

3 Claims, 4 Drawing Sheets

METHOD OF MANUFACTURING MEDICAL APPLIANCE DISPOSAL CONTAINER

CROSS REFERENCE TO RELATED APPLICATION

The present application is a continuation of Ser. No. 449,675, filed Dec. 12, 1989, now abandoned, which is a divisional application of copending application Ser. No. 300,946, filed January Jan. 24, 1989, now U.S. Pat. No. 4,927,076 issued May 22, 1990, entitled Medical Appliance Disposal Container, and assigned to the assignee of the present application.

FIELD OF THE INVENTION

The present invention relates in general to the disposal of hazardous and potentially hazardous materials and is particularly directed to a new and improved container for the safe disposal of medical appliances such as syringes, scalpel blades, laboratory culture slides, blood tubing, toxic waste vessels, etc.

BACKGROUND OF THE INVENTION

The safe disposal of hazardous and potentially dangerous medical waste, especially sharp instruments such as syringes and scalpel blades, is a paramount concern of medical facilities where both medical personnel and patients may be exposed to a threat of injury and contracting contagious disease. As a consequence, public health service organizations, such as the Center for Disease Control, have issued advisories that containers used for such disposal must be rigid, leakproof and puncture resistant Unfortunately, many of the medical waste material containers that are currently employed by the medical community are typically multi-piece plastic structures, usually of 'snap together' construction, which not only are susceptible to leaks at their joints, but often readily come apart, spilling their contents, when subjected to 'trash removal' type of handling by hospital custodial personnel. Moreover, because hospital regulations often require destruction by incineration, burning containers made substantially entirely of plastic can cause the emission of considerable quantities of toxic pollutants.

With the paramount concern of the medical community and society in general of the devastating effects of the spread of diseases such as the AIDS virus, herpes and hepatitis, the potentially life-threatening shortcomings of conventional waste disposal containers have resulted in a demand for stricter regulation and control of both methods of the disposal of medical waste and improvements in the types of containers that are used for the purpose. In addition, there is a need for an economical, efficient waste device for controlling hospital/medical costs.

Advantageously, a number of these problems are addressed by the container configurations described in my previously issued U.S. Pat. Nos. 4,410,086, 4,452,358 assigned to the assignee of the present application. In particular, the use of a unitary structure of fiberboard material and the provision of coatings to prevent liquid absorption and thereby maintain container integrity and prevent leakage are detailed. As an additional feature, such patented waste container structures are provided with needle bending and removal devices that facilitate instrument disposal and minimize risk to medical personnel during the discarding of syringes.

SUMMARY OF THE INVENTION

In accordance with the present invention, a number of the safety features that are addressed by the above-referenced patented containers are further enhanced by a new and improved medical waste disposal container, the configuration and assembly of which enables the container to either meet or exceed all of the above-mentioned safety criteria. For this purpose, like the patented containers, the present invention is comprised of a unitary body structure formed of a substantially flat sheet, that has a plurality of laminated layers of compact (non-toxic) fibrous material, such as high bond strength (on the order of 450-500 Mullen) fiberboard, which is effectively impermeable to needle punctures. The laminated sheet structure is also provided, preferably at least within its interior, with one or more thin (on the order of one to several mils) pliable layers of an absorbtion resistant material, such as polyurethane, that forms a liquid barrier and thereby prevents the passage of fluid through the entirety of the fibrous material and thus serves to maintain the integrity and strength of the wall structure of the container.

In the course of manufacture of the container, the sheet material is divided into a plurality of foldable panels that are scored, wrapped at corners and adhesively joined together to define a bottom, sidewalls and a top of the body structure. In accordance with a first aspect of the present invention, the panels are scored along lines spaced apart from folding edges thereof, so as to cause, during subsequent folding of sheet panels, the formation of beads in the sheet material that are separated from the corners of folds, whereby edges of the panels abut against corners of the folds and ensure a snug, leakproof fit of the panels.

Pursuant to a further aspect of the invention, the top of the container is formed of a first, interior panel of the sheet material having an opening therethrough that is shaped to define a lip extending from one side of the opening, and a second, outer panel of the sheet material, disposed adjacent to the first panel, the second panel having a cut therethrough to define a flexible tab overlying the opening in the first panel and being sized to effectively close the opening when urged downwardly onto the opening and engaged by the lip, and thereby assisting in the safe retention of disposed medical components, such as syringes and scalpel blades, that have been inserted through the top into the container. Like the patented containers, the interior of the container is preferably coated with an absorption resistant material to effectively provide a leakproof seal at the intersections of its sidewalls and bottom.

Pursuant to a further feature of the invention, assembly is facilitated and additional sealing of the foldable sheet portions is achieved by irradiating the laminate sheet material with electromagnetic energy, preferably from an infrared lamp, immediately prior to folding and wrapping sheet portions that are to overlap one another and joined together. This irradiation makes the thin plastic layer that forms the outer wall surface of the sheet material tacky, so that it becomes intimately bonded to an adjacent folded sheet portion to which it is joined, thus securing the wrapped sheet portions together, without the need for a separate adhesive, and providing an additional fluid barrier at the wrap joints.

When contrasted with the multi-piece construction of a conventional plastic container, the structural configuration of the present invention offers a number of advantages. First, its unitary construction effectively prevents the container from coming apart and facilitates the formation of a lip/tab closure of the opening in the top of the container that securely retains discarded component that have been inserted in the container. In addition, the high bond strength, compact (non-toxic) fiberboard within the laminate sheet material permits the container to be subjected to severe external forces without loss of structural integrity. A plastic container, on the other hand, effectively shatters into multiple pieces, releasing the entirety of its contents. Furthermore, because of the high density of the fiberboard layers of the sheet material, the container resists needle penetration, so that it effectively meets each of the requirements currently proposed for medical waste disposal containers.

DETAILED DESCRIPTION

Figure 1:
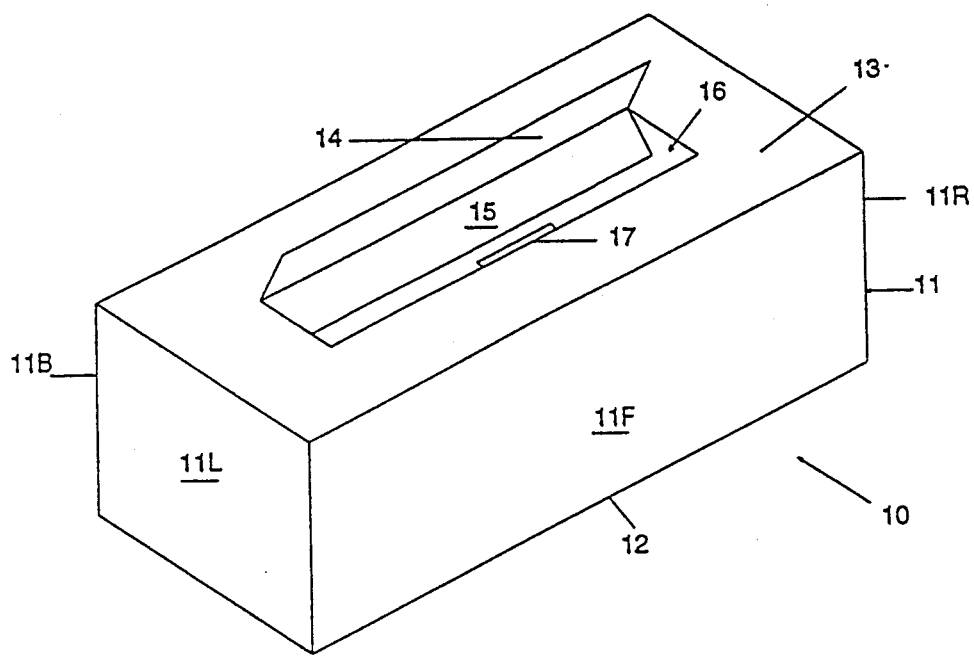
FIG. 1 is a pictorial illustration of an embodiment of a medical appliance disposal container in accordance with the present invention.

FIG. 1 diagrammatically illustrates one embodiment of a medical appliance disposal container in accordance with the present invention, comprising a generally rectangular-configured body 10 having a plurality of sides 11, a bottom 12 and a top 13. In the generally rectangular configuration shown in FIG. 1, the body has a front 11F, a pair of parallel left and right sides 11L and 11R, respectively, and a back 11B parallel with front 11F. Each of bottom 12 and top 13 is contiguous with each of the sides 11. While bottom 12 has a continuous surface, top 13 has a slot or opening 16 of sufficient size for insertion of a medical appliance, such as a needle-syringe assembly or scalpel. Slot or opening 16 is defined by an inner tab 15 which is bent or inclined downwardly into the container 10, and an outer closure tab 14 which is bent or inclined upwardly away from the top 13. The edges of the opening 16 are configured to define a lip portion 17 opposite to the edge from which tabs 14 and 15 are bent upwardly and downwardly, respectively. When closure tab 14 is urged downwardly into opening 16 against the 'spring-back' tendency created along its fold line, lip 17 serves to securely capture and retain the tab at approximately the surface of the top of the container, so that there is no tab protrusion at opening 16.

Figure 2:
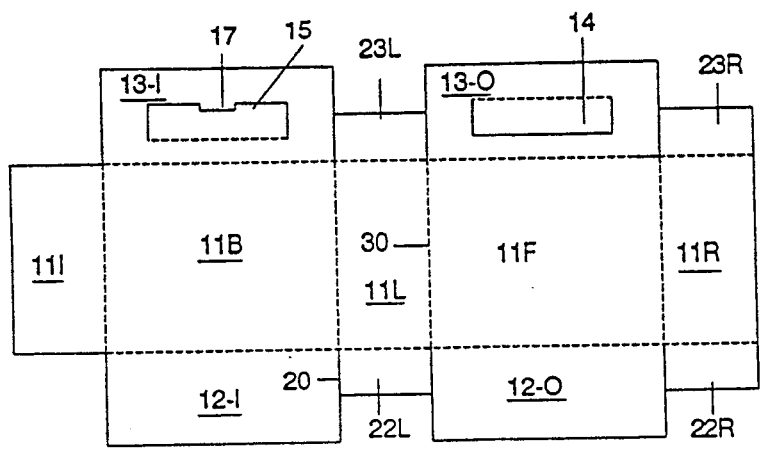
FIG. 2 shows the general layout of a laminate sheet material which is cut and fold/wrapped, so that the respective sheet portions may be assembled to form the unitary container construction of FIG. 1.

As described briefly above, because the container of the present invention is formed of unitary construction, it does not readily come apart, thus minimizing spillage of its contents. FIG. 2 shows the general layout of a laminate sheet material which is cut therethrough along solid lines 20 and fold/wrapped along broken lines 30, so that the respective panels may be assembled to form the unitary construction configuration of FIG. 1.

More specifically., the sheet layout is comprised of a right side panel 11R, a front panel 11F, a left side panel 11L, a back panel 11V and interior side panel 11I, which are successively contiguous with one another, as shown. A pair of bottom and top minor flap panels 22R and 23R extend from opposite ends of right side panel 11R. Similarly, an outer top panel 13-0 and an outer bottom panel 12-0 are contiguous with and extend from the top and bottom edges of the front panel 11F. An additional pair of minor flap panels 22L and 23L extend from the bottom and top edges of left side panel 11L, while an interior top panel 13-I extends from the top edge of back panel 11B, and an interior bottom panel 12-I extends from the bottom edge of back panel 11B.

The opening or slot 16 in the top 13 of the container is defined by cut lines in outer top panel portion 13-0, which form outer tab 14, and cut lines in the inner top panel 13-I, which form inner tab 15 and lip 17. It should be noted that the length of each of minor flap panels 23R and 23L is defined to provide a clearance between the ends of top panels 13 and the openings therein, so that the minor flap panels do not overlap the openings. The lengths of minor flap panels 22R and 22L may be somewhat longer than the lengths of minor flap panels 23R and 23L, so long as the ends of the minor panels do not overlap one another in their folded assembled condition. In its assembled condition, each of minor flap panels 22R and 22L is secured to the interior surface of interior bottom panel 12-I.

The panel layout shown in FIG. 2 is folded together such that each of minor flap panels 22R and 22L is contiguous with the interior surface of interior bottom panel 12I, the bottom surface of which, in turn, is contiguous with the interior surface of outer bottom panel 12-0. Similarly, the top surface of each of minor flap panels 23R and 23L is contiguous with the bottom surface of top interior panel 13-I, the top surface of which, in turn, is contiguous with the bottom or interior surface of top outer panel 13-0. The outer surface of interior side panel 11I is contiguous with the interior surface of right side panel 11R.

Figure 3:
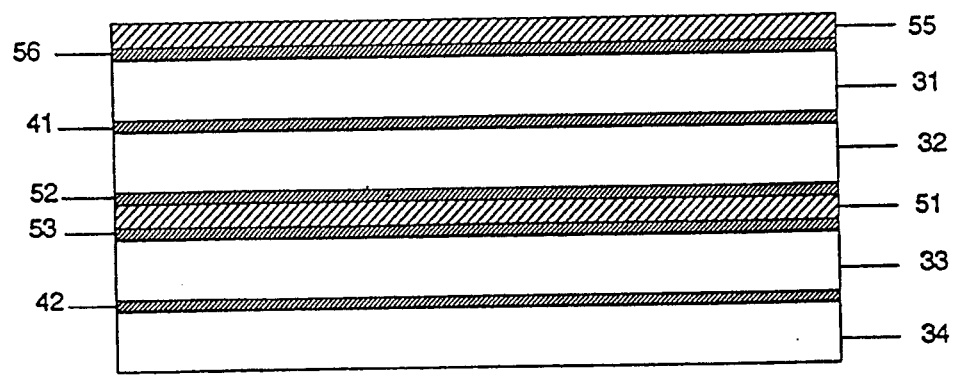
FIG. 3 shows an exaggerated diagrammatic cross-sectional illustration of fiberboard/plastic laminate sheet material that may be used for the manufacture of the medical waste disposal container in accordance with the present invention.

FIG. 3 shows an exaggerated diagrammatic cross-sectional illustration of one embodiment of the fiberboard/plastic laminate sheet material that may be used for the manufacture of the medical waste disposal container in accordance with the present invention. As shown therein, the sheet material is preferably comprised of a plurality of layers of wood pulp fiber-based fiberboard, 31, 32, 33 and 34, an individual layer having a thickness on the order of 12-25 mils. Preferably, the fiberboard is extremely high strength material such as Kraft board supplied by Sunoco Fiber Drum, having a bond strength on the order of 450-550 Mullen (e.g. 500 Mullen).

The respective fiberboard layers are adhesively laminated together using a conventional adhesive such as polyvinyl alcohol. Because of the high density, high Mullen bond strength of the fiberboard layers, the sheet material is extremely strong and is effectively needle-puncture proof. To provide a water seal barrier, one or more layers of fluid impervious material, such as a thin flexible plastic, is included as part of the laminate structure. In the cross-sectional illustration shown in FIG. 3, two such layers are shown. Specifically, an inner flexible plastic layer 51 is adhesively bonded (by way of polyvinyl alcohol adhesive layers 52 and 5) to fiberboard layers 32 and 33, respectively and an outer plastic layer 55 is adhesively bonded by way of polyvinyl alcohol adhesive layer 56, to fiberboard layer 31. If desired, an additional plastic layer may be provided on the outer surface of fiberboard layer 34. The fluid barrier-providing thin plastic layer may be formed of polyvinyl chloride or polyurethane, having a thickness on the order of 1 to several mils, so that it has elasticity. This flexible plastic material may be provided as a central or interior layer of the laminate structure, as shown at 51 in FIG. 3, and/or as the outer surface, as shown by plastic layer 55. Moreover, the plastic material is preferably a high visibility material, to provide a hazardous waste warning to medical personnel, e.g. a bright red material, or a yellow orange to provide a clear contrast background for blood spatters. Manufacture of the laminate sheet material, per se, may be effected in a conventional manner, by feeding webs from respective rolls of fiberboard and plastic sheet stock through a rolling mill lamination station whereat an adhesive applicator and compression rolling mill secure the multiple layers together.

It should also be noted that while the laminate structure shown in FIG. 3 is comprised of two pairs of fiberboard layers, the number employed is not limited to the embodiment. What is important, however, is that the structure be symmetric or "balanced". Namely, a single fiberboard layer having a layer of plastic on only one side thereof will tend to distort in one direction and not lay flat. Pairs of multiple fiberboard layers (two boards per layer being shown in FIG. 3) provide a balanced or symmetric arrangement of fiberboard layers about an intermediate thin plastic film layer, so that the sheet laminate will essentially lay flat. With an outer layer of plastic film, the overall thickness of the sheet laminate is typically on the order of 58-62 mils.

As noted above, in accordance with a preferred embodiment of the invention, the intermediate or center layer of the laminate structure comprises a thin fluid-impervious layer on either side of which a multiple fiberboard structure is formed. In addition to this centrally located fluid barrier, the outer layer of the fiberboard structure is preferably comprised of the fluid impervious plastic. By providing the thin, flexible plastic on the outer surface of the sheet material, several advantages are afforded. First of all, the resulting container surface has a non-cellular absorption resistant surface, which may be readily wiped off and thereby maintained in a disinfected condition. In addition, by the appropriate pigmentation of the plastic material, such as a bright red, the outer surface of the container will possess a high visibility coloration. In the course of manufacture, therefore, the application of an external paint merely for warning coloration purposes is unnecessary.

Figure 4:
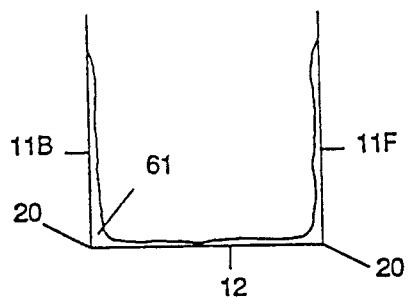
FIG. 4 diagrammatically illustrates an interior coating of an absorption resistant material formed along the interior sidewalls and the interior bottom surface of the container.

FIG. 4 diagrammatically illustrates a further feature of the present invention in which an interior coating 61 of an absorption resistant material, such as polyvinyl alcohol, is formed along the interior sidewalls and the interior bottom surface of the container. After the box has been assembled, layer 61 is formed by pouring an absorption-resistant liquid, such as a commercially available non-toxic liquid glue, through the opening 16 in the top of the container and allowing it to adhere to the sides and bottom so that it coats the fold/wrap lines 20. Alternatively or, in addition, the interior surface of the sheet material may include the above-mentioned plastic layer. Still, by providing the coating 61, the corners of the bottom and sides of the interior of the container are completely sealed after the liquid coating sets up and dries.

Figure 5:
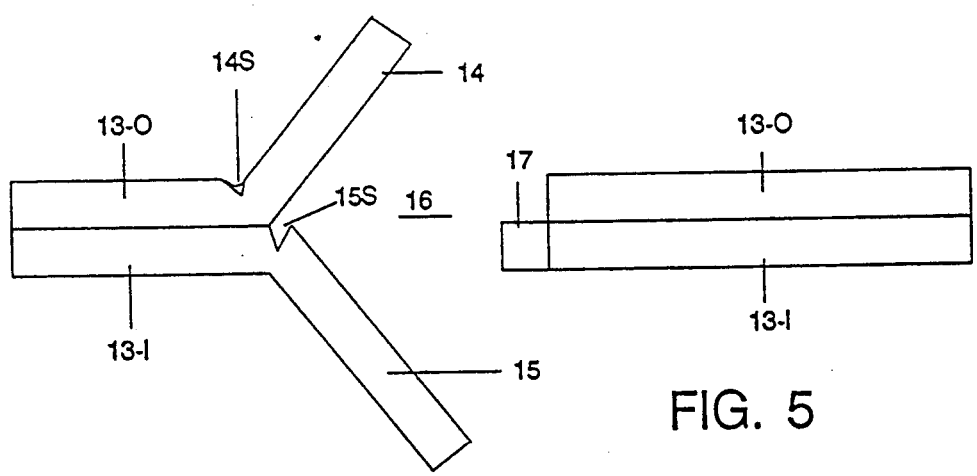
FIGS. 5 and 6 are diagrammatic cross-sectional illustrations of a portion of the top of the container whereat an opening is formed by way of an outer tab and an inner tab.
Figure 6:
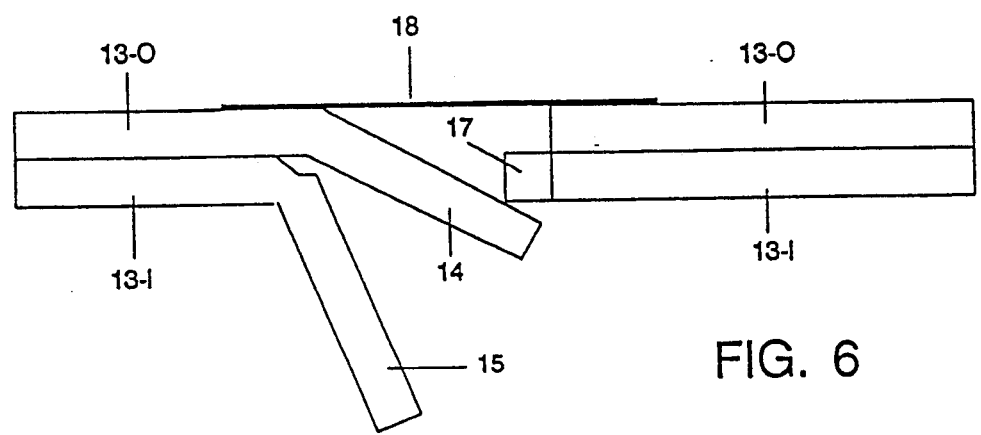

FIGS. 5 and 6 are diagrammatic cross-sectional illustrations of that portion of the top 13 of the container whereat the opening 16 is formed by way of outer tab 14 and inner tab 15. As shown at 14S in FIG. 5, the outer surface of top panel 13-0 is scored along the fold line of outer tab 14 and a slit score 15S is formed along the fold line of interior tab 15 of interior top panel 13-I. Outer tab 14 is bent or folded upwardly away from the aperture 16, whereas inner tab 15 is folded downwardly into the container. The folding down of interior tab 15 provides sufficient clearance for entry of medical waste articles into the container through the opening 16.

Because of the substantial "memory" possessed by the laminate sheet material of which the container is formed, each of tabs 14 and 15 tends to remain in its folded condition resulting from the scoring. Consequently, merely folding tab 14 down to its previous position will not cause the tab 14 to stay there. It tends to spring back. To secure outer tab 14 in a fully closed position, interior top panel 13I has a lip 17 as shown diagrammatically in FIGS. 1, 2, 5 and 6. When tab 14 is pushed inwardly into the container, it snaps past lip 17 and then is caught by its underside surface, as shown in FIG. 6, to retain outer tab 14 in a substantially closed, horizontal position. An adhesive warning/identification label that is normally provided on the outer surface of front panel IIF of the container may then be peeled off and placed over the enclosed top 14, as shown by broken lines 18 in FIG. 6, to securely close the top of the container.

Figure 7:
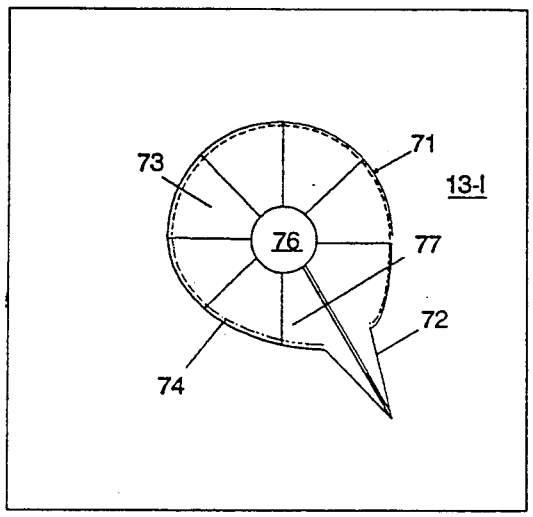
FIGS. 7 and 8 show a further embodiment of the present invention, in which the container is substantially square-shaped and provided with a generally circular aperture in its top.
Figure 8:
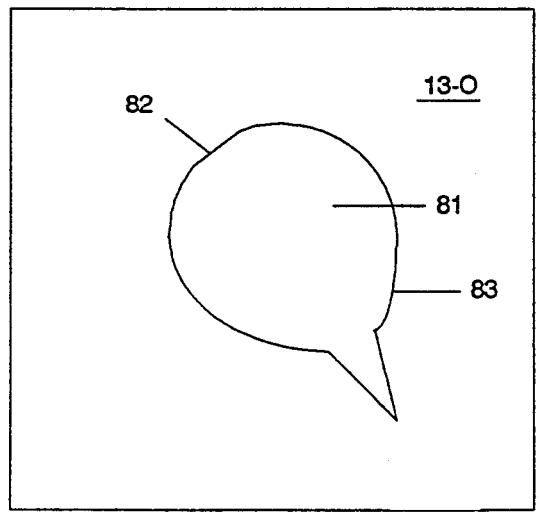

In accordance with an alternative embodiment of the present invention, the container may be substantially cube or square-shaped and provided with a generally circular aperture in the top thereof. For this purpose, as shown in FIGS. 7 and 8, the interior top panel 13-0' has a generally circular, sectioned region 71 from one portion of which extends a generally triangular or 'V'-shaped region 72. A central circular aperture 76 defines the interior edge of a plurality of generally wedge-shaped flaps 73 which are bent inwardly from a score line 74. A narrow slot 77 extends from central aperture 76 to the vertex of region 72 to provide a converging 'crimping' region whereat needles may be bent during the course of discarding of a syringe. Score line 74 follows the generally circular shape of region 71. As in the embodiment shown in FIGS. 5 and 6, slit scores 74 cause the wedge shape tabs 73 to remain in their generally downwardly bent condition.

FIG. 8 shows the configuration of the outer top panel 13-O' having an outer flap 81 which is coincident with the opening 71 within interior top panel 13-I' and extends from a score 82 along a slit line 83, which conforms with the shape of generally circular or curvilinear region 71 and 'V'-shaped region 72 of FIG. 7. Score 82 causes the outer tab 81 to be retained in a generally upwardly or outwardly extending condition, similar to tab 14 in the embodiment shown in FIGS. 5 and 6. However, unlike the generally rectangular-shaped outer tab 14 in the embodiment shown in FIG. 1, the score line 82 of the generally circular tab shown in FIG. 8 is relatively short, so that the outer tab 81, when urged down into its original position, will not tend to resist remaining in the horizontal position and can be readily sealed by an overlying plastic label, similar to that shown in FIG. 6. In other words, the need for a lip to grab tab 81 is unnecessary.

Figure 9:
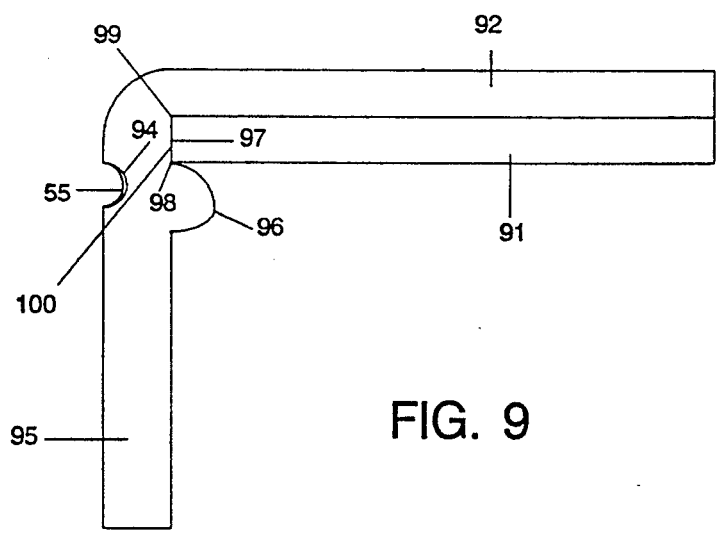
FIG. 9 shows the manner in which scoring of the sheet material of the present invention is selectively located to enable the corners to be effectively wrapped in a tight configuration.

FIG. 9 shows the manner in which scoring of the sheet material of the present invention is selectively located to enable the corners to be effectively wrapped in a very snug tight configuration, rather than folded, which might otherwise prevent a secure seal of the corners of the folds. More particularly, diagrammatically illustrated in FIG. 9 is a portion 91 of a panel around an edge 97 of which a panel 92 is to be wrapped. In accordance with the present invention, panel 92 is scored (as by means of a sharp rule edge) at region 94 which is slightly below corner 98 of panel edge 97. Because of the elasticity of pliable thin plastic layer 55, the application of a scoring rule permits panel 92 to be scored or indented as shown at 94 which, in turn, causes the protrusion of a bead 96 on portion 95 of the panel opposite the outer side whereat thin flexible plastic layer 55 is provided. When tightly wrapped around (rather than simply folded at) edge 97, because of the separation of bead 96 from corner 99 whereat panel 92 is bent to form top portion 93, edge 97 is snuggly captured by and abuts against interior surface 100 of panel portion 92. Due to the elasticity of outer plastic layer 55, the fluid impervious barrier at the corner is maintained. The placement of the score 94 below corner 98 whereat the panel is tightly wrapped or bent is to be contrasted with a conventional scoring of sheet material at the corner.

Figure 10:
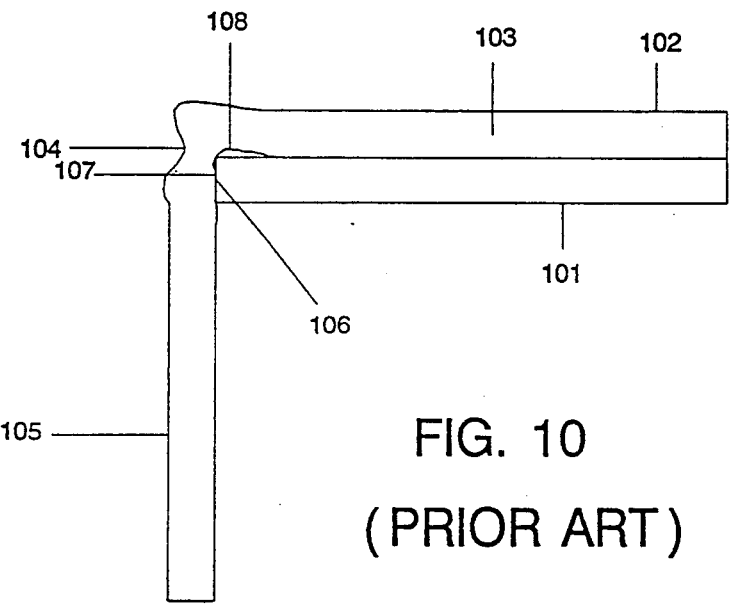
FIG. 10 shows the corner configuration of sheet material that has been conventionally scored and folded.

More particularly, as shown in FIG. 10, a conventionally scored panel 101 is shown as having an end edge 107 at which another panel 102 is to be folded into a pair of fold panel portions 103 and 105. A conventional score 104 provided at the corner causes the formation of a bead 106 is directly adjacent to and abuts against edge 107 of panel 101. Such a bead usually creates a space 108 adjacent to the edge of 107 of panel 101, rather than a snug seal when the score is offset from the corner in accordance with the present invention, as shown in FIG. 9, described above.

In addition to scoring the wrapped edges of the sheet material at locations slightly displaced from the corners of the container, so as to cause the formation of the bead around the edge of the flap, as shown in FIG. 9, rather than against the edge of the flap as shown in FIG. 10, the manufacturing process of the present invention employs a mechanism which takes advantage of the physical properties of the plastic layer that forms the outer surface of the sheet material and, consequently, the outer surface of the container. Specifically, rather than employ a separate adhesive for securing the respective panels of the layout shown in FIG. 2, for example, to form the container, the present invention exposes those panel sections which are to be joined together to a source of electromagnetic radiation, such as infrared light, which heats the plastic material to a tacky, adhesive state, so that the outer plastic layer, in effect, becomes the adhesive, thereby eliminating the need for a separate adhesive material to secure the panels of the container together.

Figure 11:
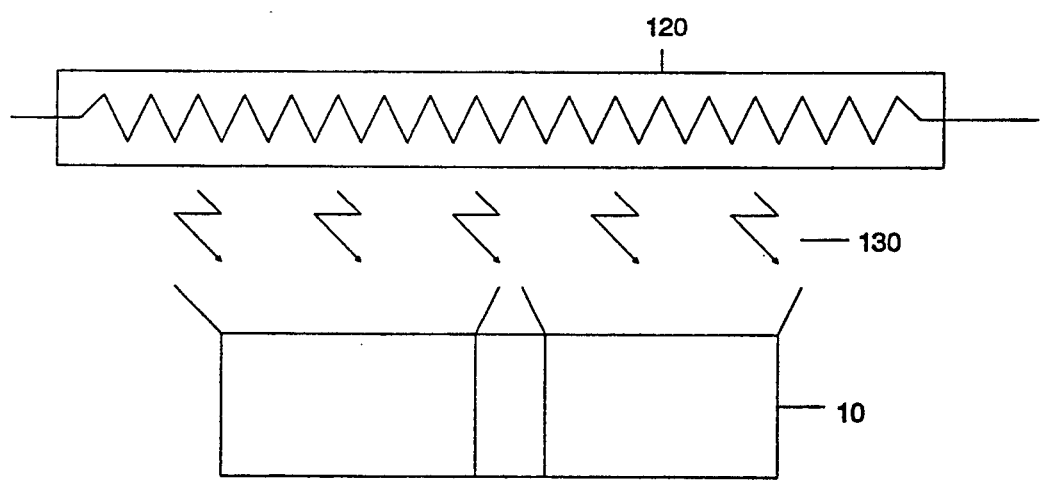
FIG. 11 diagrammatically shows the irradiation of panels and flaps of laminate sheet material, which are to be joined together to form a container illustrated in FIG. 1.

More particularly, as diagrammatically shown in FIG. 11, the respective panels and flaps of the container 10, which are to be joined together to form a structure such as that illustrated in FIG. 1, may be irradiated by electromagnetic radiation 130, such as that provided by an infrared lamp 120. Lamp 120 irradiates the outer plastic layer for a period of time on the order of five to twenty seconds, which is sufficient to soften the outer plastic layer 55 and render it tacky. The respective panels are then folded over and pressed against one another through a suitable folding medium, such as a Teflon or marble roller, which has no affinity for the plastic. Advantageously, the set-up time for such an irradiated plastic material is on the order of one to two seconds, so that the time required for the assembly of a container is reduced considerably in comparison with the case where a separate adhesive material is employed.

As will be appreciated from the foregoing description, the unitary, fluid impervious laminate structure of the container structure according to the present invention is capable of satisfying critical safety criteria for medical waste containers. Not only is the laminate structure effectively impermeable to punctures, but, due to the presence of one or more layers of absorbtion resistant pliable material, and the coating of its interior with an absorption resistant material, yields a container that is effectively leakproof. In addition, by irradiating the foldable sheet portions of the container with infrared light, the thin plastic layer that forms the outer wall surface of the sheet material effectively becomes a strong adhesive, which intimately bonds adjacent folded sheet together, thus simplifying the manufacturing process and providing an additional fluid barrier at the wrap joints.

While I have shown and described several embodiments in accordance with the present invention, it is to be understood that the same is not limited thereto but is susceptible to numerous changes and modifications as known to a person skilled in the art, and I therefore do not wish to be limited to the details shown and described herein but intend to cover all such changes and modifications as are obvious to one of ordinary skill in the art.

What is claimed:

1. A method of making a container comprising the steps of:
    (a) providing a substantially flat sheet material having a laminated structure containing compact fibrous material and an outer layer of material that is effectively impervious to the passage of fluid therethrough and which, when irradiated by infrared rays for a prescribed period of time, becomes tacky;
    (b) forming, in the sheet material provided in step (a), a plurality of foldable panels that are to be folded and joined together to define bottom, sidewall and top portions of a body;

(c) irradiating said sheet material with infrared electromagnetic energy so as to heat said outer layer to its tacky condition; and (d) folding and joining together sheet panels that have been irradiated in step (c), whereby folded and joined together sheet panels are bonded to one another by means of the outer layer of said sheet material, so as to form said container;

(e) coating interior intersections of bottom and sidewall portions of said body with fluid absorption resistant material; and (f) prior to step (d), scoring said foldable panels of sheet material along lines spaced apart from folded corners thereof, so as to cause, during the folding of sheet panels in step (d), the formation of beads in said sheet material that are separated from the corners of fold in said sheet material, wherein the scoring of a respective one of said foldable panels of sheet material comprises scoring said respective one of said foldable panels of sheet material on one side thereof at a region adjacent to a fold location so as to cause the protrusion of a bead on an opposite, interior side of said respective one of said foldable panels of sheet material, such that a side edge of a respective one of said foldable panels of sheet material abuts against an interior fold corner of another of said foldable panels of sheet material that is folded to be contiguous therewith and is captured between said bead and interior folded corner of said another of said foldable panels of sheet material, thereby effectively providing a sealed joint thereat and preventing the formation of a leakage space between the interior of said container and the exterior thereof.

2. A method of making a container comprising the steps of:

(a) providing a substantially flat sheet material having a laminated structure containing compact fibrous material and a thin outer layer of pliable material that is effectively impervious to the passage of fluid therethrough;

(b) forming, in the sheet material provided in step (a), a plurality of foldable panels that are to be folded and joined together to define bottom, sidewall and top portions of said body;

(c) scoring said foldable panels of sheet material along lines spaced apart from folding regions thereof, so as to cause, during subsequent folding of sheet panels, the formation of beads in said sheet material that are separated from the corners of folds in said sheet material, wherein the scoring of a respective one of said foldable panels of sheet material comprises scoring said respective one of said foldable panels of sheet material on one side thereof at a region adjacent a fold location so as to cause the protrusion of a bead on an opposite, interior side of said respective one of said foldable panels of sheet material, such that a side edge of a respective one of said foldable panels of sheet material abuts against an interior fold corner of another of said foldable panels of sheet material when folded to be contiguous therewithin and is captured between said bead and said interior fold corner of said another of said foldable panels of sheet material, thereby effectively providing a sealed joint thereat and preventing the formation of a leakage space between the interior of said container and the exterior thereof;

(d) irradiating said sheet material with infrared electromagnetic energy so as to heat said thin outer layer of pliable material to a tacky condition; and (e) folding and adhesively joining together sheet panels that have been scored in step (c) and irradiated by infrared electromagnetic energy to a tacky condition in step (d), whereby folded and joined together sheet panels are bonded to one another, so as to form said container.

3. A method according to claim 2, further including the step of:

(f) coating interior intersections of bottom and sidewall portions of said body with fluid absorption resistant material.

* * * * *